US011607423B2

(12) United States Patent
Dalgleish et al.

(10) Patent No.: US 11,607,423 B2
(45) Date of Patent: Mar. 21, 2023

(54) COMBINATION OF A CANNABINOID AND A CHEMOTHERAOPEUTIC AGENT FOR THE TREATMENT OF BREAST CANCER

(71) Applicant: Akos Biosciences, Inc., Naples, FL (US)

(72) Inventors: Angus Dalgleish, London (GB); Wai Liu, London (GB); Nadine Hall, London (GB)

(73) Assignee: Akos Biosciences, Inc., Naples, FL (US)

( * ) Notice: Subject to any disclaimer, the term of this patent is extended or adjusted under 35 U.S.C. 154(b) by 57 days.

(21) Appl. No.: 17/044,534

(22) PCT Filed: Apr. 4, 2019

(86) PCT No.: PCT/EP2019/058550
§ 371 (c)(1),
(2) Date: Oct. 1, 2020

(87) PCT Pub. No.: WO2019/193112
PCT Pub. Date: Oct. 10, 2019

(65) Prior Publication Data
US 2021/0030779 A1 Feb. 4, 2021

(30) Foreign Application Priority Data

Apr. 4, 2018 (EP) .................................... 18165731

(51) Int. Cl.
| | | |
|---|---|---|
| *A61K 31/7068* | (2006.01) |
| *A61P 35/00* | (2006.01) |
| *A61K 9/00* | (2006.01) |
| *A61K 31/05* | (2006.01) |
| *A61K 31/337* | (2006.01) |
| *A61K 31/352* | (2006.01) |
| *A61K 31/704* | (2006.01) |

(52) U.S. Cl.
CPC ........ *A61K 31/7068* (2013.01); *A61K 9/0056* (2013.01); *A61K 31/05* (2013.01); *A61K 31/337* (2013.01); *A61K 31/352* (2013.01); *A61K 31/704* (2013.01); *A61P 35/00* (2018.01)

(58) Field of Classification Search
CPC .. A61K 31/7068; A61K 31/05; A61K 31/337; A61K 31/352; A61K 31/704; A61K 31/7048; A61K 9/0056; A61P 35/00
See application file for complete search history.

(56) References Cited

U.S. PATENT DOCUMENTS

2013/0209483 A1* 8/2013 McAllister ............. A61K 45/06
514/393

FOREIGN PATENT DOCUMENTS

GB 2478595 A 9/2011

OTHER PUBLICATIONS

Moulder et al., Clinical Pharmacology & Therapeutics, 2008, 83, p. 26-36. (Year: 2008).*
Mannila et al., Journal of Pharmaceutical Sciences, 2007, 92(2), p. 312-319. (Year: 2007).*
International Search Report and Written Opinion of the International Searching Authority dated Jun. 13, 2019 International Application No. PCT/EP2019/058550; European Patent Office; Rijswijk, Netherlands.
Elbaz, Mohamed M et al article entitled "A novel role of transient receptor potential vanilloid type 2 (TRPV2) for augmentation of chemotherapeutic drug efficacy in triple-negative breast cancer;" Jul. 31, 2015; Cancer Research, American Association for Cancer Research; vol. 75, No. Suppl. 15, p. 3487; US.
Ward, Sara Jane et al. article entitled "Cannabidiol inhibits paclitaxel-induced neuropathic pain through 5-HT 1A receptors without diminishing nervous system function or chemotherapy efficacy: Cannabidiol prevents chemotherapy neuropathic pain;" Jan. 13, 2014; British Journal of Pharmacology; vol. 171, No. 3, pp. 636-645; UK.
Caffarel, Maria M. et al article entitled "Cannabinoids: A new hope for breast cancer therapy?" Nov. 1, 2012; Dancer Treatment Reviews; vol. 38, No. 7, pp. 911-918; Amsterdam, NL.
Scott, Katherine A. et al; article dated Mar. 22, 2017; "Anticancer effects of phytocannabinoids used with chemotherapy in leukaemia cells can be improved by altering the sequence of their administration"; International Journal of Oncology 51; pp. 369-377.
Communication pursuant to Article 94(3) EPC dated Aug. 26, 2022; European Application No. 19715914.8; European Patent Office; Munich, Germany.

* cited by examiner

*Primary Examiner* — Jonathan S Lau
(74) *Attorney, Agent, or Firm* — Stevens & Showalter LLP

(57) ABSTRACT

The present invention in the field of cancer therapeutics is based on the finding (illustrated in FIG. 4) that when cannabinoids are administered to cancer cells after a chemotherapeutic agent has been administered, the combined treatment leads to lower cancer cell viability than administration of the chemotherapeutic agent alone. There is provided a pharmaceutical composition comprising a chemotherapeutic agent for use in the treatment of breast cancer, wherein said treatment comprises a first phase in which the chemotherapeutic agent is administered, and a subsequent second phase in which a cannabinoid is administered.

17 Claims, 4 Drawing Sheets

COMBINATION OF A CANNABINOID AND A CHEMOTHERAOPEUTIC AGENT FOR THE TREATMENT OF BREAST CANCER

FIELD OF THE INVENTION

The invention relates to regimes of drug administration and drug combinations for use in the treatment of breast cancer.

BACKGROUND TO THE INVENTION

Breast cancer is the most common cancer in women worldwide, and is the cause of significant pain and distress to sufferers and their families. It manifests in the unregulated over-proliferation of cells in the breast, often starting in the ducts or lobules, and can progress into metastasis, serious complications, and death.

Some instances of breast cancer are susceptible to chemotherapeutic treatment, in which drugs are administered which disrupt this over-proliferation of cells. However, because cancer cells contain largely the same proteins and other targets as the healthy cells in the body, there are few cancer-specific druggable targets, and chemotherapies often simply target all quickly proliferating cells in the body. As such, while these chemotherapies can be successful in suppressing tumours, there are side effects associated with them, and these become more severe the higher the dose of the chemotherapy.

Numerous proteins have been implicated in the aberrant cellular processes associated with breast cancer. Protein Kinase RNA-like Endoplasmic Reticulum Kinase (pERK) is a kinase of the endoplasmic reticulum which is involved in stress-signalling pathways. As tumours with high levels of this protein tend to respond less favourably to treatment, it has been seen as a negative prognostic indicator for breast cancer progression.

SUMMARY OF THE INVENTION

It has been found by the present inventors that when cannabinoids are administered to cancer cells after a chemotherapeutic agent has been administered, the combined treatment leads to lower cancer cell viability than administration of the chemotherapeutic agent alone. As levels of pERK, a negative prognostic indicator for breast cancer, are increased by cannabinoids, such an effect is contrary to expectations.

According to a first aspect of the invention, there is provided a pharmaceutical composition comprising a chemotherapeutic agent for use in the treatment of breast cancer, wherein said treatment comprises a first phase in which the chemotherapeutic agent is administered, and a subsequent second phase in which a cannabinoid is administered.

According to a second aspect of the invention, there is provided a pharmaceutical composition comprising a cannabinoid for use in the treatment of breast cancer, wherein said treatment comprises a first phase in which a chemotherapeutic agent is administered, and a subsequent second phase in which the cannabinoid is administered.

According to a third aspect of the invention, there is provided a pharmaceutical composition comprising a cannabinoid for use in the treatment of breast cancer in a subject, wherein the subject has previously been administered a chemotherapeutic agent.

According to a fourth aspect of the invention, there is provided a pharmaceutical formulation comprising a chemotherapeutic agent and a cannabinoid for use in the treatment of breast cancer, wherein the chemotherapeutic agent and cannabinoid are formulated or incorporated so as to facilitate sequential administration.

DETAILED DESCRIPTION OF THE INVENTION

The present inventors have found that when a cannabinoid is administered to breast cancer cells after administration of a chemotherapeutic agent, the viability of the breast cancer cells is reduced compared to the case in which just the chemotherapeutic agent is administered.

Figure 1:
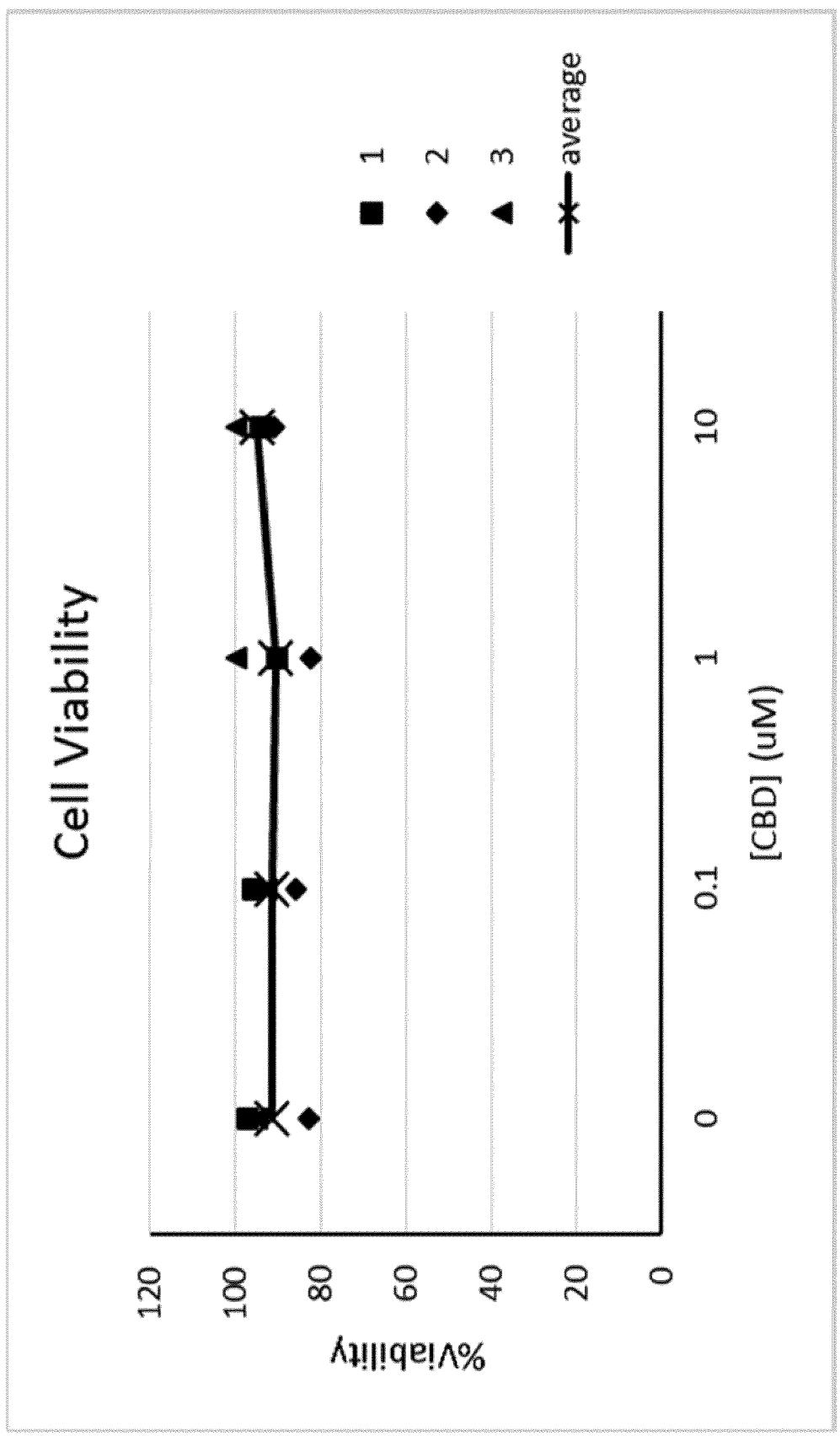
FIG. 1 plots the percentage viability of MCF7 breast cancer cells presented with differing levels of cannabidiol (CBD), as measured according to example 1.
Figure 2:
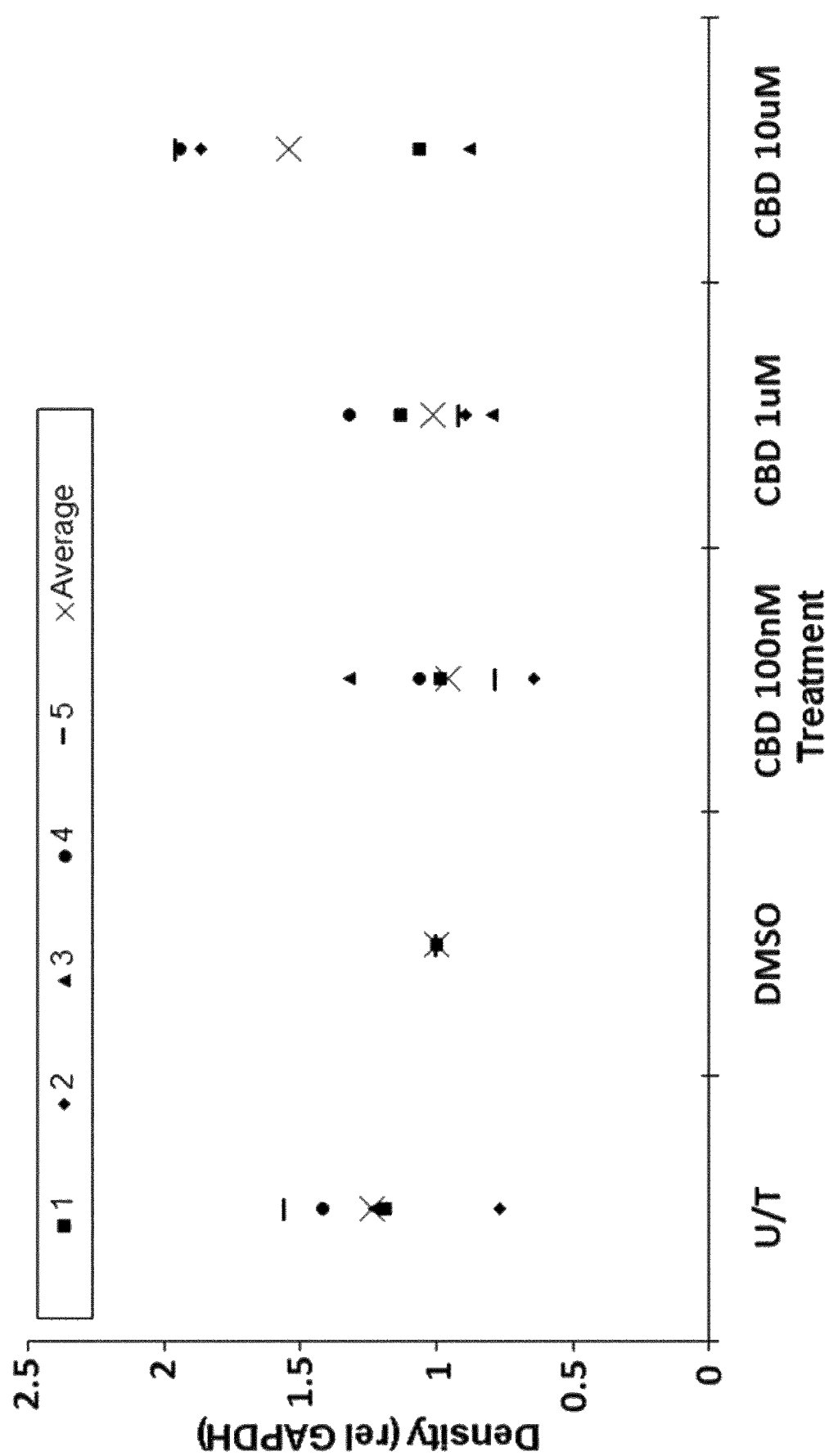
FIG. 2 plots the relative levels of Protein Kinase RNA-like Endoplasmic Reticulum Kinase (pERK) in MCF7 breast cancer cells presented with differing levels of CBD, as measured according to example 2.

This unexpected discovery runs up against traditional thinking surrounding Protein Kinase RNA-like Endoplasmic Reticulum Kinase (pERK), which has until now been seen as a negative prognostic indicator for breast cancer. Traditionally, cancer cells with high levels of pERK are seen as more likely to survive and proliferate than those with lower levels. Cannabinoids have no effect on cancer cell viability in isolation, as seen in FIG. 1, and in fact even increase the concentration of pERK in breast cancer cells, as seen in FIG. 2.

Figure 4:
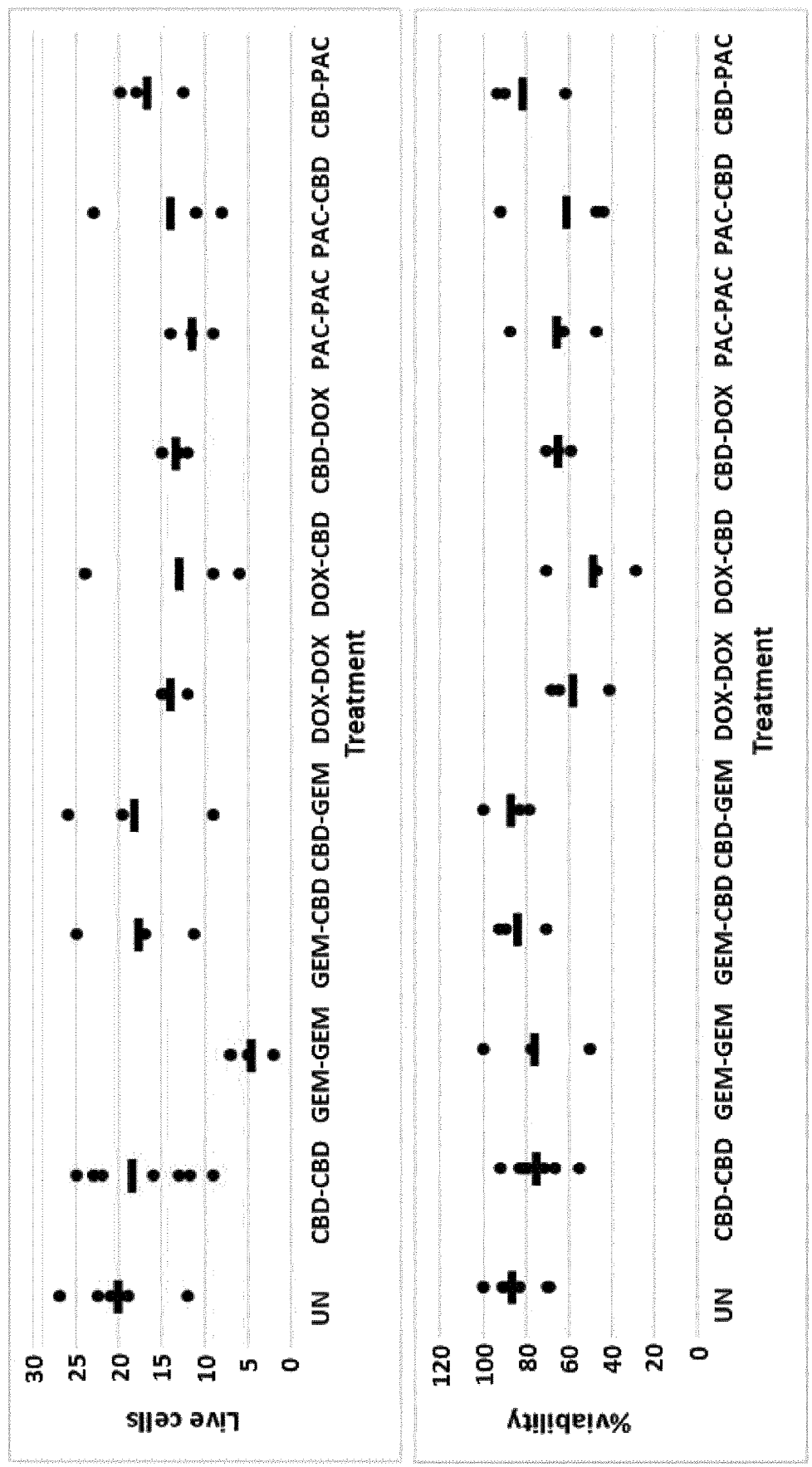
FIG. 4 plots the viability and live cell count relative to control of MCF7 breast cancer cells presented for two days with either CBD or one of the representative chemotherapeutic agents, then put into fresh media containing another of the compounds for a further two days. The compound presented in the first two days is before the dash, and the later compound is after the dash. CBD=Cannabidiol, GEM=Gemcitabine, DOX=Doxorubicin, PAC=Paclitaxel, as measured according to example 4.

As such they would be expected to be poor breast cancer treatments. However, when administered as part of the current invention, cannabinoids increase the potency of the chemotherapeutic agent they follow, as illustrated in FIG. 4.

As the chemotherapeutic agents of the current invention may, like most chemotherapy, cause unpleasant side-effects in patients, the ability to provide the same or greater therapeutic effect with a smaller overall dose of the chemotherapeutic agent minimises the risk and severity of side-effects in subjects.

Each of the aspects of the invention is aimed towards the treatment of breast cancer, and the treatment comprises two phases. In the first phase a chemotherapeutic agent is administered, and in the subsequent second phase a cannabinoid is administered.

As used herein, the terms "treating" and "treatment" and "to treat" refer to both therapeutic measures that cure, slow down, and/or halt progression of a diagnosed pathologic condition or disorder, and also to prophylactic or preventative measures that prevent and/or slow the development of a targeted pathologic condition or disorder. Therefore, those in need of treatment include those already with the disorder, those prone to have the disorder, and those in whom the disorder is to be prevented. In some instances, a subject is successfully "treated" for a tumour/cancer according to the present invention if the subject shows one or more of the following: a reduction in the number of, or complete absence of, cancer cells; a reduction in the tumour size; inhibition of, or an absence of, cancer cell infiltration into peripheral organs including, for example, the spread of cancer into soft tissue and bone; inhibition of, or an absence of, tumour metastasis; inhibition of, or an absence of, tumour growth; reduced morbidity and mortality; reduction in tumourigenicity, tumourigenic frequency, or tumourigenic capacity of a tumour; reduction in the number or frequency of cancer stem cells in a tumour; differentiation of tumourigenic cells to a non-tumourigenic state; or some combination of effects. Inasmuch as the treatment comprises two phases, the phases may be separated geographically and overseen by different health professionals.

As used herein, the term "tumour/cancer" refers to any mass of tissue, however small, that results from excessive cell growth, proliferation and/or survival, either benign (noncancerous) or malignant (cancerous), including precancerous lesions. Any form of breast cancer is envisaged.

As used herein, "breast cancer" refers to any mass of tissue that results from excessive cell growth, proliferation and/or survival of the breast tissue of men or women, including, for example, carcinomas and sarcomas. The breast cancer may be, for example, invasive breast cancer, invasive ductal breast cancer, invasive lobular breast cancer, triple negative breast cancer, inflammatory breast cancer, angiosarcoma of the breast, ductal carcinoma in situ (DCIS), lobular carcinoma in situ (LCIS), tubular carcinoma, medullary carcinoma, alveolar carcinoma, solid variant carcinoma, signet ring cell carcinoma, metaplastic carcinoma, or mucinous carcinoma. Breast cancer may also refer to lobular neoplasia, lobular hyperplasia, and other pre-cancerous conditions.

The term "invasive cancer" refers to cancer that has spread beyond the primary tumour in which it developed, and is growing in surrounding, healthy tissues. Invasive cancer is sometimes referred to as infiltrating cancer. The term is intended to include all primary invasive breast cancers including, invasive ductal carcinoma "not otherwise specified" (IDC) and IDC subtypes (e.g. mixed, pleomorphic, osteoclast types), invasive lobular carcinoma (ILC), tubular carcinoma, mucinous carcinoma, medullary carcinoma, neuroendocrine tumours, invasive papillary and cribriform carcinoma and invasive apocrine, metaplastic and oncocytic subtypes.

The breast cancer may be at any stage of progression. The treatment of the current invention may be used on subjects with stage 1A breast cancer or those with stage 1B breast cancer. It may be used on subjects with stage 2A breast cancer or those with stage 2B breast cancer. It may be used on subjects with stage 3A breast cancer or those with stage 3B breast cancer, or those with stage 3C breast cancer. It may also be used on subjects with stage 4 breast cancer. At any of these stages, the breast cancer may be relapsed or recurrent breast cancer, in which the cancer returns after a period of improvement or remission.

Cancer treatments are often particularly effective on subsets of tumours expressing particular biomarkers, and the breast cancer to be treated by the current invention may be characterised by its expression of various biomarkers. The subject may have a tumour which has been clinically tested and shown to be positive or negative for clinically relevant levels of one or more biomarkers selected from estrogen receptor α (ERα), estrogen receptor β (ERβ), progesterone receptor, Ki67, HER2, p53, ARF, TBX2, TBX3, cyclin D1, cyclin E, BRCA1, BRCA2, and VEGF.

As used herein, "clinically relevant levels" refer to expression levels of a given gene which may serve to characterise the cancer as belonging to a particular clinical category. Different clinical categories of cancer exhibit different molecular abnormalities, and may be most effectively treated in differing ways, as such the ability to accurately categorise tumours increases the efficacy of treatment.

When the breast cancer is in a subject, the subject may be any animal susceptible to the pathology, including but not limited to humans, non-human primates, horses, canines, felines, and rodents.

In the first phase of the treatment, a chemotherapeutic agent is administered to the breast cancer, or to the subject having breast cancer. This chemotherapeutic agent may be any chemotherapeutic agent, but is preferably an anthracycline, a taxane, or a nucleoside analogue. The agent may be any pharmaceutically acceptable salt, or prodrug of the above, and administration may be via any acceptable route, potentially chosen from such routes as the oral, buccal, sublingual, nasal, pulmonary, intravenous, intraperitoneal, intramuscular, rectal, vaginal, topical, intraocular and/or transdermal routes. Any combination of the above chemotherapeutic agents is also envisaged. Any vehicle including albumin and castor oil is envisaged for each of the chemotherapeutic agents.

Also envisaged is any formulation or administration device which incorporates a chemotherapeutic agent and a cannabinoid in such a way that the two are sequentially released as per the invention. This may be, for example, a pill or other formulation with two differentially structured compartments, or the two agents pre-incorporated into two different materials with different release rates, it may be an implanted device with differentially situated compartments or drug-soaked areas, or it may be a device which is electronically programmed to inject each at particular intervals.

The dosage regime of the chemotherapeutic agent is not particularly limited, but preferable regimens are envisaged for different chemotherapeutic agents. Preferably the chemotherapeutic agent of the current invention is an anthracycline, a taxane, or a nucleoside analogue. Where ranges are given herefrom, they may be read as approximate, and are inclusive of the range boundaries.

For anthracyclines administration may be such that the concentration within the patient is generally within the range of 0.1-10 nM, preferably within the range of 0.5 nM-5 nM, more preferably within the range of 0.8-2 nM, or it may be such that the concentration within the patient is generally within the range of 10 nM-1 µM, preferably within the range of 50-500 nM, more preferably within the range of 80-200 nM. The anthracycline may be administered at any physiologically acceptable dose, preferably at a dose of 10-90 mg/m$^2$, more preferably 30-70 mg/m$^2$, yet more preferably 40-60 mg/m$^2$, most preferably 45-55 mg/m$^2$.

Anthracyclines may be administered at any physiologically allowable frequency. For example an anthracycline may be administered intravenously once every three weeks, once every two weeks, once a week, once every other day, or once a day. Preferably anthracyclines are administered once a week, more preferably once every three weeks.

The anthracycline may be any, for example daunorubicin, doxorubicin, epirubicin, idarubicin, valrubicin, nemorubicin, pixantrone, or sabarubicin, and is preferably doxorubicin.

For taxanes, administration may be at any dose but is preferably such that the concentration within the patient is generally within the range of 0.1-10 nM, preferably within the range of 0.5-5 nM, more preferably within the range of 0.8-2 nM, or it may be such that the concentration within the patient is generally within the range of 10 nM-1 µM, preferably within the range of 50-500 nM, more preferably within the range of 80-200 nM. Taxanes may be administered at any physiologically acceptable dose, preferably at 50-260 mg/m$^2$, more preferably 100-210 mg/m$^2$, even more preferably 125-185 mg/m$^2$, yet more preferably 135-175 mg/m$^2$, most preferably 150-160 mg/m$^2$. Taxanes may be administered at any physiologically allowable frequency. For example a taxane may be administered once every three weeks, once every two weeks, once a week, once every other day, or once a day.

The taxane may be any, for example, paclitaxel, nab-paclitaxel, CrEL-paclitaxel, paclitaxel poliglumex, cationic liposomal paclitaxel, polymeric-micellar paclitaxel, DHA-paclitaxel, docetaxel, cabazitaxel, abraxane, DJ-927, BMS-184476, larotaxel, taxotere, hongdoushan A, B, or C, and is preferably paclitaxel.

As used herein, "nucleoside analogue" refers to a chemotherapeutic agent having a mechanism of action which relies on the agent, or a downstream metabolite of the agent, substituting for a nucleoside or nucleotide in a biochemical reaction, or otherwise disrupting the addition of a nucleoside or nucleotide into a polynucleotide chain. Agents which are analogues of nucleic acid precursors are also envisaged. As such, it will be appreciated that nucleotide analogues as well as precursor analogues also form part of the group of nucleoside analogues.

For nucleoside analogues administration is preferably such that the concentration within the patient is generally within the range of 1-100 µM, preferably 5-50 µM, more preferably 8-20 µM. Nucleoside analogues may be administered at any physiologically allowable dose but are preferably administered at a dose of 250-2,250 mg/m$^2$, more preferably 500-2,000 mg/m$^2$, even more preferably 800-1,700 mg/m$^2$, yet more preferably 1,100-1,400 mg/m$^2$, most preferably 1,200-1,300 mg/m$^2$. They may be administered at any physiologically allowable frequency, and are preferably administered once a week, more preferably once every three weeks.

The nucleoside analogue may be any encompassed compound, for example, gemcitabine, azacitidine, azathioprine, capecitabine, doxifluridine, fluorouracil, hydroxyurea, mercaptopurine, methotrexate, tioguanine, DHAC, zebularine, cytosine arabinoside. Preferably the nucleoside analogue is gemcitabine.

In a medical setting, it is envisaged that the dose and administration frequency of the chemotherapeutic agent may be adjusted on a case-by-case basis depending on the status and needs of the patient, and the progress of the treatment up to the point of administration.

In the subsequent second phase of the treatment regimen, a cannabinoid is administered.

Cannabinoids are a class of compounds understood by the skilled person which comprise those abundantly made by plants of the *Cannabis* genus, as well as endocannabinoids which are synthesised in animals. Synthetic compounds which are structurally similar to natural cannabinoids and/or are active against cannabinoid receptors are also envisaged.

Cannabinoids exert various effects on the physiology of mammalian and tumour cells, and many of these effects are mediated by two G protein-coupled receptors known as cannabinoid receptors and deemed CB1 and CB2. These receptors are known to interact with at least five structurally distinct classes of compounds. These include the plant-derived classical cannabinoids, such as tetrahydrocannabinol and cannabinol; the non-classical bicyclic cannabinoid agonists, such as CP55,940; the endogenous cannabinoid agonists, such as anandamide (AEA); the aminoalkylindole (AAI) agonists, such as WIN55,212-2; and the antagonist/inverse agonists, such as SR141716A (Pertwee, 1995). Each class of compound is envisaged within the term cannabinoid, and each class may be useful for treating different aspects of breast cancer.

As the compounds can be agonistic or antagonistic, and some are more active against CB1, while others more active against CB2, compounds may be directed towards treatment of specific stages and categories of breast cancer. For example, some may bind specifically to CB2, such as JWH-133, and some may bind specifically to CB1, such as SR141716A. In certain pathologies, CB1 agonists may be desired, in others CB1 antagonists may be more appropriate. Alternatively or additionally, CB2 agonists and/or antagonists may be selected for use in the treatment of the current invention.

The cannabinoid of the current invention may be derived from a natural source, or be produced synthetically. The term "cannabidiol" (CBD) as used herein refers to a phyto-cannabinoid produced by *Cannabis* species. In some embodiments the cannabinoid used in the present invention is in a purified form, in a composition having at least 95% purity when the solvent is not counted. In other embodiments, the cannabinoid is a component of a plant extract, which may be administered to a subject. In some embodiments, a plant extract comprises, excluding the solvent, 10% to 95% cannabinoid. In some embodiments, a plant extract comprises 20% to 80% cannabinoid. In some embodiments, a plant extract comprises 30% to 70% cannabinoid. In some embodiments, a plant extract comprises 40% to 60% cannabinoid. The cannabinoid may be a botanical drug substance (BDS), defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." The cannabinoid is preferably cannabidiol (CBD).

The cannabinoid may be derived from a plant extract, and/or itself be a plant extract comprising one or more cannabinoid selected from one or more of the following categories of plant cannabinoids: Cannabigerol-type (CBG), cannabichromene-type (CBC), cannabidiol-type (CBD), cannabinodiol-type (CBND), tetrahydrocannabidiol-type (THC), cannabinol-type (CBN), cannabitriol-type (CBT), cannabielsoin-type (CBE), isocannabinoids, cannabicyclol-type (CBL), cannabicitran-type (CBT), cannabichromanone-type (CBCN).

The cannabinoid may also be a highly purified or chemically modified substance derived from natural sources. In some cannabinoids, for example CBD, it may comprise chemically modified derivatives of fully-decarboxylated cannabinoid which retain desired activity, or more preferably natural derivatives exhibiting improved activity which are produced according to standard principles of medicinal chemistry. In some embodiments, fully-decarboxylated CBD derivatives may exhibit a lesser degree of activity than the starting material so long as they retain sufficient activity to be therapeutically effective or exhibit improvements in properties desirable in pharmaceutically active agents such as improved solubility, enhanced uptake or reduced toxicity.

When used herein the term can refer to any cannabinoid, but the cannabinoid is preferably selected from the list containing cannabidiol, tetrahydrocannabinol, cannabidiolic acid, cannabinol, cannabigerol, cannabivarin, tetrahydrocannabivarin, cannabidivarin, cannabichromene, arachidonoylethanolamine, 2-arachidonoylglycerol, 2-arachidonoyl glyceryl ether, N-arachidonoyl dopamine, virodhamine, dronabinol, nabilone, rimonabant, anandamide, R-(+)-Met-anandamide, WIN-55,212-2, HU-210, JWH-133, SR144528, SR141716A, CP55,940 or combinations thereof, or pharmaceutically acceptable salts, solvates, hydrates, stereoisomers, clathrates, prodrugs, and analogues thereof which bring about equivalent effects.

The cannabinoid may be administered at conventional amounts based on the particular cannabinoid and the details of the particular case. In certain embodiments, the cannabinoid is to be administered once a day at a dose of between 50 mg and 1000 mg, preferably between 200 mg and 800 mg, more preferably between 300 mg and 500 mg, most preferably between 350 mg and 450 mg. The cannabinoid may be administered at any frequency, for example, twice a day, three times a day, every other day, every third day, or every fourth day. Preferably the cannabinoid is administered daily. In a medical setting, it is envisaged that the dose and administration frequency may be adjusted on a case-by-case basis depending on the status and needs of the patient, and the progress of the treatment up to the point of latest administration.

The method of administration is not particularly limited for cannabinoids, and they may be administered via the oral, buccal, sublingual, nasal, pulmonary, intravenous, intraperitoneal, intramuscular, rectal, vaginal, topical, intraocular and/or transdermal routes, preferably being administered sublingually. When the cannabinoid is administered via the pulmonary route, it may be via inhalation of a vapour comprising cannabinoids, optionally mediated by combustion or vaporisation of cannabinoid-comprising plant matter.

This second phase of the treatment, in which the cannabinoid is administered, may last for any period of time, including indefinitely. It could alternatively last four weeks, three weeks, or two weeks, but is preferably carried out for a period of from 1 to 7 days, more preferably 1 to 3 days.

Once the second phase is complete, it is envisaged that in some circumstances the first phase will recommence, optionally followed again by the second phase, that is, numerous cycles of treatment may be necessary.

There may be a "recovery phase" in between the end of the first treatment phase and the start of the second treatment phase. During the recovery phase no chemotherapeutic agent or cannabinoid is administered. The recovery phase may be any length of time, may have a duration of, for example, a day, two days, or three days, and is preferably no more than a week. Also envisaged in the recovery phase is the situation in which a clinician decides to reduce the dose or administration frequency based on the status and needs of the patient, and the extent to which the treatment is being effective.

Also envisaged is a method of treating breast cancer wherein said method comprises a first phase in which a chemotherapeutic agent is administered, and a subsequent second phase in which a cannabinoid is administered.

Further envisaged is the use of a chemotherapeutic agent and a cannabinoid for the manufacture of a medicament for the treatment of breast cancer, wherein said chemotherapeutic agent is to be administered in a first phase, and said cannabinoid is to be administered in a subsequent second phase.

EXAMPLES

Example 1

The breast cancer cell line MCF7, growing exponentially, was reset at a concentration of $1\times10^4$/ml and allowed to adhere overnight. Cannabidiol (CBD) was added at 0.1, 1, or 10 µM, and cell viability assessed after 48 h by cell counting, using the dye trypan blue to discriminate dead from live cells, the results of which are displayed in FIG. 1.

As the viability of the cancer cells was similarly high at all administered concentrations, including 0, the evidence suggests that the viability of cancer cells is unaffected by CBD in this range. As such, it appears that cannabinoids do not have a direct cytotoxic effect on breast cancer cells. Therefore if a cannabinoid is used in conjunction with another agent, and an effect on cancer viability is seen which is different to the effects of the other agent alone, then these effects must stem from some form of mechanistic interaction between the cannabinoid and the other agent.

Example 2

The breast cancer cell line MCF7, growing exponentially, was reset at a concentration of $1\times10^4$/ml and allowed to adhere overnight. Cannabidiol (CBD) was added at 100 nM, 1 µM, or 10 µM, and cells were harvested for standard western blotting techniques after 48 h. Immunoprobing was performed using anti-pERK antibodies, and the densities of each band determined. These values were then expressed relative to a GAPDH loading control. The data are displayed in FIG. 2, and show the individual data points for 5 separate experiments.

As can be seen, relative to the controls, pERK was increased in cells exposed to higher levels of CBD. As pERK is traditionally seen as a negative prognostic indicator for cancer progression, one would predict from this data that CBD would increase the viability and proliferation of cancer cells.

Example 3

Figure 3:
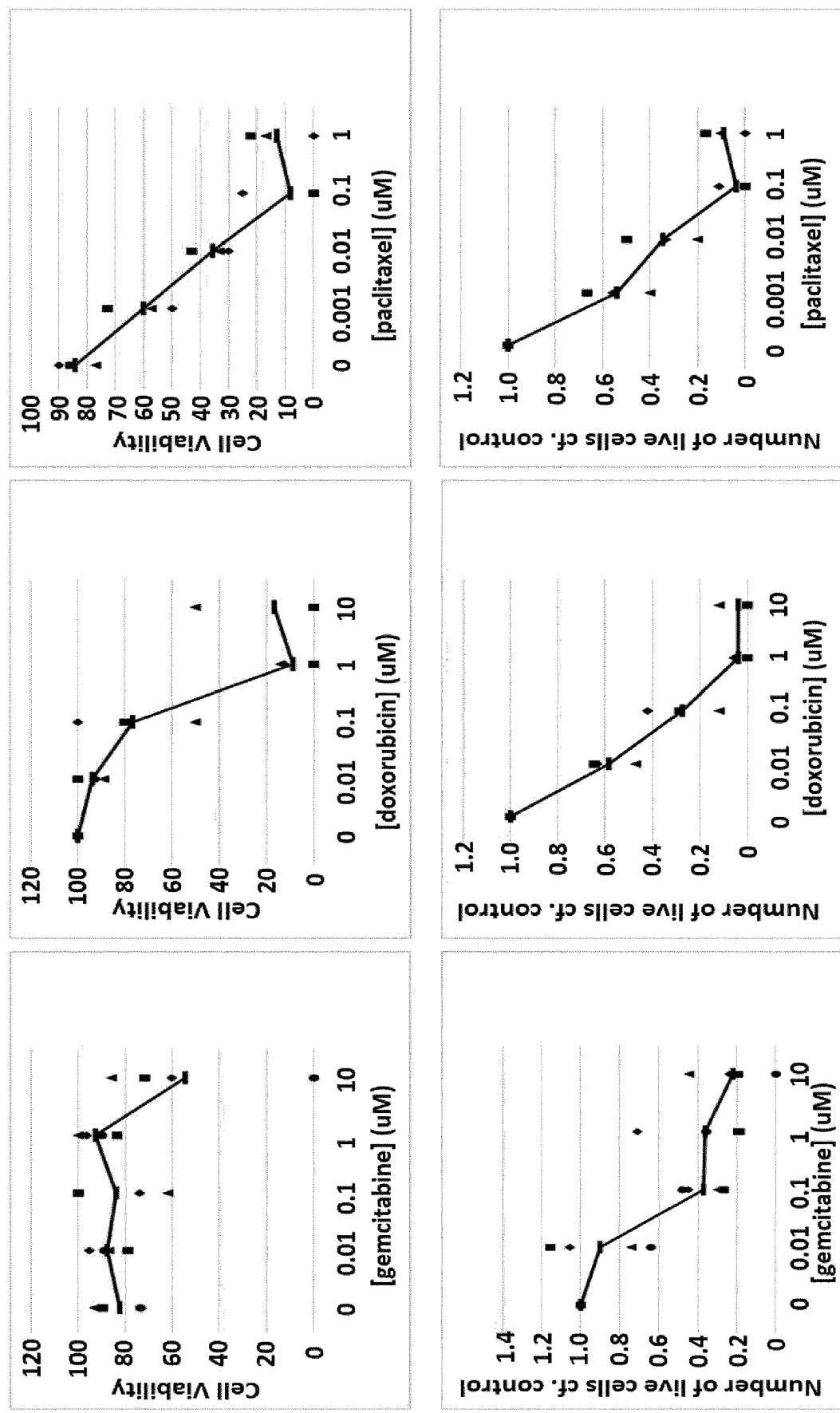
FIG. 3 plots the viability and live cell count relative to control of MCF7 breast cancer cells presented with varying concentrations of three representative chemotherapeutic agents, as measured according to example 3.

The breast cancer cell line MCF7, growing exponentially, was reset at a concentration of $1\times10^4$/ml and allowed to adhere overnight. Either gemcitabine, doxorubicin or paclitaxel was added, at 0.01, 0.1, 1, or 10 µM for gemcitabine and doxorubicin, and 0.001, 0.01, 0.1, or 1 µM for paclitaxel. Cell viability was assessed after 48 h by cell counting, using the dye trypan blue to discriminate dead from live cells. The data are displayed in FIG. 3, and confirm that the concentrations used in example 4 are appropriate.

Example 4

The breast cancer cell line MCF7, growing exponentially, was reset at a concentration of $1\times10^4$/ml and allowed to adhere overnight. A treatment schedule was then employed that involved two rounds of treatment each lasting 48 h, meaning a complete treatment schedule would be over 96 h. For the first round of treatment, either CBD (10 μM), gemcitabine (GEM: 10 μM), doxorubicin (DOX: 100 nM) or paclitaxel (PAC: 1 nM) was added to the cells and they were left to grow for 48 h. After this time, exhausted media was removed and replaced with fresh medium supplemented with any of the drugs as listed earlier. After a further 48 h, cell viability was assessed by cell counting, using the dye trypan blue to discriminate dead from live cells. The data are displayed in FIG. 4.

The data reveal a number of surprising trends. Firstly, the order of administration of the chemotherapeutic agent and cannabinoid has a notable effect on the viability and live cell count of the treated cancer cells. In all cases, the cancer treatment administering a chemotherapeutic agent as a first agent, followed by a cannabinoid, delivers similar or superior results to the case in which they are administered the other way around.

A further surprising result is that in many cases, treatment with a chemotherapeutic agent followed by a cannabinoid offers superior results to double treatment with a chemotherapeutic agent, even though such a treatment amounts to administering just half the dose of chemotherapeutic agent over the course of the experiment. Given that CBD was shown in FIG. 1 to be inactive in treating cancer in isolation, and is known to produce fewer unpleasant side-effects than the chemotherapy agents tested herein, such a treatment can be expected to provide similar or superior cancer-suppressing results to chemotherapeutic agents alone, with less severe side effects.

REFERENCES

Pertwee et al. (1995)—*Life Sci.* 1995; 56(23-24):1949-55.

The invention claimed is:

1. A method for the treatment of breast cancer, wherein said treatment comprises a first phase in which a chemotherapeutic agent is administered, and a subsequent second phase in which a cannabinoid is administered, wherein administration of the cannabinoid is carried out after a recovery phase lasting from 1 to 7 days, during which neither the chemotherapeutic agent nor the cannabinoid is administered.

2. The method of claim 1, wherein the subject has previously been administered a chemotherapeutic agent.

3. The method of claim 1, wherein the chemotherapeutic agent is selected from the list consisting of anthracyclines, taxanes, and nucleoside analogues, and pharmaceutically acceptable salts and prodrugs thereof.

4. The method of claim 3, wherein the chemotherapeutic agent is doxorubicin, paclitaxel, or gemcitabine.

5. The method of claim 4, wherein the doxorubicin is administered to a subject at a dose of 40-60 mg/m$^2$, the paclitaxel is administered to a subject at a dose of 135-175 mg/m$^2$, and the gemcitabine is administered to a subject at a dose of 1,100-1,400 mg/m$^2$.

6. The method of claim 5, wherein the doxorubicin is administered to a subject at a dose of 45-655 mg/m$^2$, the paclitaxel is administered to a subject at a dose of 150-160 mg/m$^2$, and the gemcitabine is administered to a subject at a dose of 1,200-1,300 mg/m$^2$.

7. The method of claim 1, wherein the cannabinoid is selected from the list consisting of cannabidiol, tetrahydrocannabinol, cannabidiolic acid, cannabinol, cannabigerol, cannabivarin, tetrahydrocannabivarin, cannabidivarin, cannabichromene, arachidonoylethanolamine, 2-arachidonoylglycerol, 2-arachidonoyl glyceryl ether, N-arachidonoyl dopamine, virodhamine, dronabinol, nabilone, rimonabant, anandamide, R(+)-Met-anandamide, WIN-55, 212-2, HU-210, JWH-133, SR144528, SR141716A, CP55, 940, or combinations thereof.

8. The method of claim 7, wherein the cannabinoid is cannabidiol.

9. The method of claim 8, wherein the cannabidiol is administered to a subject at a dose of 50-1,000 mg.

10. The method of claim 9, wherein the cannabidiol is administered to a subject at a dose of 300-500 mg.

11. The method of claim 1, wherein administration of the chemotherapeutic agent is to be carried out once every three weeks or once a week.

12. The method of claim 1, wherein administration of the cannabinoid is carried out once a day for a period of from 1 to 7 days.

13. The method of claim 1, wherein administration of the cannabinoid is sublingual.

14. The method of claim 1, wherein the recovery phase comprises a first recovery phase and wherein said treatment further comprises a third phase in which the chemotherapeutic agent is administered and a subsequent fourth phase in which the cannabinoid is administered, wherein administration of the cannabinoid in the subsequent fourth phase is carried out after a second recovery phase lasting from 1 to 7 days, during which neither the chemotherapeutic agent nor the cannabinoid is administered.

15. The method of claim 14, wherein a dosage of at least one of the chemotherapeutic agent or the cannabinoid is changed during the second recovery phase.

16. The method of claim 14, wherein a duration of the second recovery phase is different from a duration of the first recovery phase.

17. A method for the treatment of any stage of breast cancer, comprising administering to a subject suffering from any stage of breast cancer an effective amount of a pharmaceutical composition or a pharmaceutical formulation comprising a chemotherapeutic agent and a cannabinoid, wherein the chemotherapeutic agent and cannabinoid are formulated or incorporated so as to facilitate sequential administration, wherein administration of the cannabinoid is carried out after a recovery phase lasting from 1 to 7 days, during which neither the chemotherapeutic agent nor the cannabinoid is administered.

* * * * *